United States Patent
Lorentz et al.

(10) Patent No.: US 8,481,014 B2
(45) Date of Patent: Jul. 9, 2013

(54) POLYORGANOSILOXANE WITH A PIPERIDINE FUNCTION, DEVOID OF TOXICITY UPON CONTACT WITH THE SKIN, AND USE THEREOF IN COSMETIC COMPOSITIONS

(75) Inventors: Gilles Lorentz, Lyons (FR); Richard Vivier, Lyons (FR); Kamel Ramdani, Tupin et Semons (FR); Bernard Hendrickx, Tramoyes (FR)

(73) Assignee: Bluestar Silicones SAS, Lyon Cedex (FR)

( * ) Notice: Subject to any disclaimer, the term of this patent is extended or adjusted under 35 U.S.C. 154(b) by 354 days.

(21) Appl. No.: 12/681,021

(22) PCT Filed: Oct. 2, 2008

(86) PCT No.: PCT/EP2008/063247
§ 371 (c)(1),
(2), (4) Date: Oct. 11, 2010

(87) PCT Pub. No.: WO2009/047212
PCT Pub. Date: Apr. 16, 2009

(65) Prior Publication Data
US 2011/0020249 A1    Jan. 27, 2011

(30) Foreign Application Priority Data
Oct. 7, 2007  (FR) ...................................... 07 06892

(51) Int. Cl.
*C08G 77/26* (2006.01)
(52) U.S. Cl.
USPC ...................... 424/70.122; 424/70.12; 528/38
(58) Field of Classification Search
USPC .............................. 528/38; 424/70.122, 70.12
See application file for complete search history.

(56) References Cited

U.S. PATENT DOCUMENTS

| | | | |
|---|---|---|---|
| 2,970,089 A | 1/1961 | Hunt et al. | |
| 3,668,161 A | 6/1972 | Nauman et al. | |
| 3,773,740 A | 11/1973 | Szabo | |
| 3,853,672 A | 12/1974 | Gordon et al. | |
| 3,928,300 A | 12/1975 | Hagberg | |
| 4,195,169 A | 3/1980 | Priddy | |
| 4,294,652 A | 10/1981 | Newman | |
| 4,383,972 A | 5/1983 | McCurdy et al. | |
| 4,537,954 A | 8/1985 | Ando et al. | |
| 4,565,647 A | 1/1986 | Llenado | |
| 5,350,813 A | 9/1994 | Skilbeck | |
| 5,380,822 A | 1/1995 | Skilbeck | |
| 5,453,158 A | 9/1995 | Cummings et al. | |
| 5,540,813 A | 7/1996 | Sosa et al. | |
| 5,691,445 A | 11/1997 | Krupinski et al. | |
| 5,721,297 A * | 2/1998 | Gay et al. | ......................... 524/99 |
| 5,861,474 A | 1/1999 | Weller et al. | |
| 5,874,525 A | 2/1999 | Krupinski et al. | |
| 6,410,683 B1 | 6/2002 | Craig | |
| 6,605,577 B1 | 8/2003 | Harrison et al. | |
| 6,642,194 B2 * | 11/2003 | Harrison et al. | ............. 510/122 |
| 2004/0197287 A1 | 10/2004 | Kaczvinsky, Jr. et al. | |

FOREIGN PATENT DOCUMENTS

| | | |
|---|---|---|
| CA | 1201952 | 3/1986 |
| EP | 0665258 | 8/1995 |
| FR | 2848829 | 6/2004 |
| FR | 2886145 | 12/2006 |
| WO | 96/30421 | 10/1996 |
| WO | 97/33561 | 9/1997 |
| WO | 98/01478 | 1/1998 |
| WO | 98/58974 | 12/1998 |
| WO | 99/03894 | 1/1999 |
| WO | 99/31144 | 6/1999 |
| WO | 00/75207 | 12/2000 |
| WO | 01/42312 | 6/2001 |
| WO | 02/10223 | 2/2002 |
| WO | 02/26836 | 4/2002 |
| WO | 03/066007 | 8/2003 |
| WO | 03/088939 | 10/2003 |

* cited by examiner

*Primary Examiner* — Margaret Moore
(74) *Attorney, Agent, or Firm* — Baker Donelson Bearman Caldwell & Berkowitz, PC

(57) ABSTRACT

The invention relates to polyorganosiloxanes containing, per molecule, at least one siloxyl unit substituted with at least one group having one or more sterically hindered piperidinyl functional groups, devoid of toxicity upon contact with the skin. The invention also relates to an improved cosmetic composition comprising the polyorganosiloxanes according to the invention and the use of these compositions for the treatment of keratin materials, in particular the skin and the hair.

15 Claims, No Drawings

POLYORGANOSILOXANE WITH A PIPERIDINE FUNCTION, DEVOID OF TOXICITY UPON CONTACT WITH THE SKIN, AND USE THEREOF IN COSMETIC COMPOSITIONS

CROSS REFERENCE TO RELATED APPLICATIONS

This application is a §371 National Stage Application of PCT/EP2008/063247 filed Oct. 2, 2008, which claims priority to French Application 0706892 filed Oct. 7, 2007.

BACKGROUND OF THE INVENTION

1. Field of the Invention

The present invention relates to novel polyorganosiloxanes containing, per molecule, at least one siloxyl unit substituted with at least one group having one or more sterically hindered piperidinyl functional groups, devoid of toxicity upon contact with the skin.

The present invention also relates to an improved cosmetic composition comprising the polyorganosiloxanes according to the invention and the use of these compositions for the treatment of keratin materials, in particular the skin and the hair.

2. Description of Related Art

Numerous cosmetic compositions comprise polyorganosiloxanes ("silicones"). Polyorganosiloxanes may be used to provide a conditioning effect on the hair or the skin. Polyorganosiloxanes may also be used for sensory effects, termed cosmetic effects, during their application to the skin, the hair or the lips.

Accordingly, it has been proposed to use, in cosmetic compositions, polyorganosiloxanes of numerous different chemical structures, which may optionally contain different functional groups.

Linear polydimethylorganosiloxanes (PDMS) may be used as sensory agents on the skin, as protecting agents which act as a barrier against water, as defoaming agents, as agents for removing creamy whiteness from cosmetic compositions appearing during a first rubbing on the skin or the hair "desoapers", as conditioners and as emollients.

Cosmetic compositions comprising aminated polyorganosiloxanes have also been described, often in combination with benefits in terms of coloration. The presence of aminated groups improves the affinity of polyorganosiloxane for the hair and provides good conditioning of the hair, for compositions intended to be rinsed off or not to be rinsed off.

For example, the documents U.S. Pat. No. 6,605,577 (Chemsil Silicones Inc.), U.S. Pat. No. 6,642,194 (Chemsil Silicones Inc.), WO 03/088939 (The Procter & Gamble Company), WO 03/066007 (Dow Corning), describe cosmetic compositions comprising a polyorganosiloxane bearing specific functional groups.

In the entire description, the expression "keratin materials" will be understood to mean the materials to be cosmetically or dermatologically treated, chosen from the skin, the scalp, the hair, the eyelashes, the eyebrows, the nails and the mucous membranes.

In the entire description, the expression "leave-in" cosmetic or dermatological product will be understood to mean any product whose application to the keratin materials to be treated is not followed by rinsing with water.

In the entire description, "rinse-off" cosmetic or dermatological product will be understood to mean any product whose application to the keratin materials to be treated is followed by rinsing with water.

Numerous compositions for washing keratin materials have been described in the prior art. Accordingly, patent application FR-A-2 848 829 describes detergent compositions essentially intended for washing the hair, which exhibit improved cosmetic properties, in particular in terms of disentanglement, smoothing, suppleness, malleability and softness of the hair. These compositions comprise at least one amphoteric surfactant alkylamphohydroxyalkyl sulfonate, and at least one silicone chosen from nonorganomodified silicones having a viscosity ranging from 500 $mm^2/s$ to 1 000 000 $mm^2/s$ and organomodified silicones.

Patent application CA-1 201 952 describes surfactant compositions intended for the formulation of cosmetic compositions, in particular shampoos, whose foaming power is improved. These compositions comprise:
- from 3.75 to 15% by weight of an anionic surfactant such as a lauryl ether sulfate,
- from 1 to 4.20% by weight of an amphoteric surfactant such as an alkyl amidobetaine,
- from 0.7 to 3% by weight of a nonionic surfactant such as a polyoxyethylenated sorbitan, and
- from 0.1 to 4% by weight of a "soap" chosen from fatty acids, alkyl isethionates, alkyl taurides and alkyl sarcosides.

Patent application US 2004/0197287 describes antidandruff shampoos whose detergent and antidandruff properties have been improved. These compositions comprise:
- from 5 to 50% by weight of a detergent surfactant,
- from 0.1 to 4% by weight of an antidandruff agent,
- from 0.1 to 50% by weight of a fatty acid ester, and polyoxyethylenated sorbitan, and
- at least 20% by weight of water.

Patent application WO 97/33561 describes cleansing compositions for the hair and the skin, which exhibit a low degree of eye irritation. These compositions comprise:
- from 5 to 20% by weight of a mixture of surfactants including a nonionic surfactant, an amphoteric surfactant and an anionic surfactant, and
- from 0.01 to 3% by weight of a humectant agent, such as in particular a cationic polyol.

Finally, patent application FR-A-2 886 145 describes compositions for washing keratin materials, in particular the hair, comprising, in a cosmetically acceptable aqueous medium, at least one anionic, nonionic or amphoteric detergent surfactant, at least one cationic polymer and at least one aminated silicone comprising an amine functional group carried by a sterically hindered group. These compositions make it possible to improve the properties of visual and tactile smoothness of the hair, while having good washing and foaming power.

It is known in the prior art that certain components of cosmetic or healthcare products, such as chemical preservatives, perfumes, colorings, chemical sunscreens, ethanol and the like, can cause problems of skin irritation and/or intolerance, or even problems of contact allergy. Sensitive or reactive skins are skins which easily react to allergens or irritants following skin permeability disorders linked to impairment of the barrier function of the stratum corneum and a disequilibrium in the production of epidermal cytokines. Modification of skin permeability gives rise to the appearance of subjective and objective signs.

The appearance of the objective signs is particularly observed during the use of common cosmetic or healthcare products. They are defined by sensations of itching, tightness, prickling, heat, stinging and burning. The objective signs are revealed in an irregular manner by xerosis, by seborrhoeic dermatitis, by telangiectasia, by scales, by a blotch, by vesicles or by an edema.

According to specialists, the subjective and objective signs may appear for a short period immediately after the application of the cosmetic product, or may appear transiently, or alternatively may last longer, for the whole day or intermittently during the day. Accordingly, these signs may be discrete or severe and may require medical advice.

Accordingly, the compositions described in the prior art may exhibit certain inadequacies. In particular, the highest performing shampoos can cause prickling in the eye when the dilute product runs into the ocular sphere, which occurs frequently in children. Moreover, a good number of these shampoos may cause in people with sensitive skin reactions of discomfort, such as blotches, itching or prickling. That may be the case for certain amino silicones comprising an amine functional group carried by a sterically hindered group and described for example in patent application FR-A-2 886 145. These amino silicones, more commonly called "silicones HALS", may exhibit problems of skin sensitization and are classified as sensitizers "R43". Now, cosmetic raw materials exhibiting a skin sensitization character are restricted to very limited usage depending on the countries (see for example for Europe: European Cosmetics Directive No. 76/768/EEC).

For example, in Europe, according to the criteria of Annex VI of the Directive 67/548/EEC in its 28th adaptation to technical progress (2001/59/EC), a chemical substance or preparation is classified as a skin sensitizer "R43" when it can cause sensitization upon contact with the skin. The sensitization upon contact with the skin must have been observed in a significant number of people or via an appropriate test on animals.

Several test methods thus exist using guinea pigs: the Magnusson & Kligman or Buehler tests. Recently, the "Local Lymph Node Assay" (LLNA) test was validated and adopted by the scientific community and presented in the form of the OECD Guideline 429 or of the method described in annex V of the directive 67/548/EEC in its 29th adaptation to technical progress (2005/73/EC). This test is performed on mice and is based on the induction of the proliferation of lymphocytes in the ganglions subjacent to the site of application of the substance. The results determine whether the raw material tested should be classified as sensitizer R43.

SUMMARY OF THE INVENTION

The applicant has now discovered, surprisingly, novel polyorganosiloxanes containing, per molecule, at least one siloxyl unit substituted with at least one group having sterically hindered piperidinyl functional group(s), devoid of toxicity upon skin contact and which, when formulated in particularly smooth and nonaggressive cosmetic compositions, exhibit good qualities for use and excellent detergent and cosmetic properties.

DETAILED DESCRIPTION OF A PREFERRED EMBODIMENT

The first subject of the present invention is therefore polyorganosiloxanes A devoid of toxicity upon skin contact, containing, per molecule, at least one siloxyl unit substituted with at least one functional group V comprising at least one sterically hindered piperidinyl functional group, said polyorganosiloxanes A being characterized in that, after their preparation, the level of monomers, oligomers and polymers having a molecular mass M<1000 Daltons is reduced to a value less than 1% relative to the total molecular distribution by means of a technique allowing selective separation of the monomers, oligomers and polymers having a molecular mass M<1000 Daltons (with 1 Dalton=1 g/mol).

Accordingly, the novel polyorganosiloxanes A according to the invention exhibit the advantage, as long as the level of monomers, oligomers and polymers having a molecular mass M<1000 Daltons is reduced to a value less than 1% relative to the total molecular distribution, of no longer being classified as "sensitizer R43" and can therefore be used in the cosmetic field without restriction. Indeed, when they are formulated in cosmetic compositions, the latter therefore no longer exhibit reactions of discomfort on the skin and the scalp, and possess an excellent level of eye tolerance. In parallel, they possess cleansing properties of a good level and excellent cosmetic properties, especially a good level of softness as regards keratin materials such as the skin, the scalp, the hair, the eyelashes, the eyebrows, the nails or the mucosae skins, the hair, and in addition to this good level of softness, good properties of disentanglement and/or smoothness in the case of hair.

The selective separation of the monomers, oligomers and polymers having a molecular mass M<1000 Daltons in a mixture of silicone oils may be carried out for example by means of a technique called "devolatilization". This technique is generally used in the field of the purification of polymers. Indeed, in a process for the manufacture of a silicone polymer, the polymerization reaction should in theory be complete and convert the entire monomer to a polymer. In reality, it is known that a polymerization reaction is never complete, in particular in a solution or mass polymerization process, in particular because of the increase in the viscosity of the polymerization medium during the reaction. Accordingly, in practice, the polymer obtained generally contains residual volatile compounds such as the unreacted monomer, one or more solvents added or accumulated during the reaction, and oligomers formed during the reaction. This technique consists of a polymer degassing operation. It is carried out by subjecting the hot polymer, in particular in the form of a solution or a molten mass, to a reduced pressure, preferably a pressure below atmospheric pressure (or subatmospheric pressure), in one or more flash tanks, also called "devolatilizers", arranged in series and under successively higher vacuums. In particular, the polymer may be extruded in a flash tank in the form of a molten mass and divided, for example in the form of "falling strands", in order to facilitate the separation between the residual volatile compounds and the polymer which is thus recovered, free of these compounds. Such degassing processes are described for example in the American patents U.S. Pat. No. 2,970,089, U.S. Pat. No. 3,853,672, U.S. Pat. No. 3,928,300, U.S. Pat. No. 4,294,652, U.S. Pat. No. 4,383,972, U.S. Pat. No. 5,453,158, U.S. Pat. No. 5,540,813 and U.S. Pat. No. 5,874,525.

During the preparation of polyorganosiloxanes functionalized with sterically hindered piperidinyl groups, a standard devolatilization step (temperature between 150 and 200° C., pressure between 3 and 10 mbar for 1 to 2 h) is generally performed and the level of oligomers having a molecular mass M<1000 Daltons is always greater than 1% of the total molecular distribution (generally this level is of the order of 2 to 2.5% of the total molecular distribution).

Accordingly, all the polyorganosiloxanes functionalized with sterically hindered piperidinyl groups (for example "silicones HALS") available on the market always exhibit a level of oligomers having a molecular mass M<1000 Daltons greater than 1.5% of the total molecular distribution (generally this level is of the order of 2 to 2.5% of the total molecular distribution).

It is important to understand that, for the purposes of the invention, persons skilled in the art will continue the devolatilization step for a sufficiently long period (for example for standard temperature and pressure conditions: temperature between 150 and 200° C. and pressure between 3 and 10 mbar, the devolatilization time will be from 3 to 9 h instead of 1 to 2 h for a standard devolatilization). The devolatilization time will be determined according to the operating conditions (temperature, pressure, etc.) so that up to less than 1% of the total molecular distribution has a molecular mass M<1000 Daltons, it being possible to determine the level by the customary measuring techniques such as for example gel permeation chromatography (GPC).

According to a first variant, it is also possible to add an inert and volatile agent to the polymer. This agent is generally known under the term foaming or blowing or stripping agent, or devolatilization-assisting fluid or devolatilization aid. Under these conditions, the degassing of the polymer consists in expanding the mixture resulting from this addition, in the hot state and under reduced pressure, in a flash tank such as those previously described. The result of this expansion is that the stripping agent forms a large number of bubbles inside the molten polymer and that the stripping by diffusion of the residual volatile compounds contained in the polymer is facilitated by the considerably increased surface area of the resulting foaming mass. Examples of a stripping agent are described in American patents U.S. Pat. No. 3,668,161, U.S. Pat. No. 3,773,740, U.S. Pat. No. 4,195,169, U.S. Pat. No. 4,537,954, U.S. Pat. No. 5,350,813, U.S. Pat. No. 5,380,822 and 20 U.S. Pat. No. 6,410,683. They are generally fluids that are liquid under normal conditions and are easily volatile under the degassing conditions, such as for example water, alcohols or ketones, or a solution of carbon dioxide in water. In American patents U.S. Pat. No. 5,691,445 and U.S. Pat. No. 5,861,474, it has been proposed to replace these conventional stripping agents with a supercritical fluid which would be normally gaseous under the injection conditions, but which is maintained in solution in the polymer by virtue of high pressures applied during the injection. Accordingly, it has for example been proposed to use nitrogen, carbon dioxide and alkanes, in particular $C_4$ to $C_6$ alkanes.

In the field of silicones, depending on the viscosity of the products, it is possible to use various apparatus and processes for the selective separation of the components to be removed.

According to a preferred embodiment, the reduction of the level of monomers, oligomers and polymers having a molecular mass M<1000 Daltons is carried out by means of a batch reactor, a falling film evaporator, a scraped film evaporator, a centrifugal evaporator or a continuous flash evaporator.

A batch reactor is a reactor that is mechanically stirred by a moving body, for example a fork, a ribbon, propellers and/or turbines containing the liquid mass to be purified and is heated by its outer wall (double jacket or shell). Heat exchangers may be added to the reactor, for example in the form of coils. A suitable gas dispensing device may allow the injection of incondensable gas. The dome of the reactor is equipped with a condenser and connected to a vacuum pump. The operation consists in heating, optionally reducing the pressure and condensing the volatiles as they evaporate from the liquid mass. The longer the operating time, the purer the product.

The falling film evaporators are suitable for products having an average viscosity. The fluid is continuously poured over a heated wall so as to generate a layer of low thickness which is called film. The advantage of the film is that the vapor which forms crosses the liquid layer all the more easily if it is thin. The film progresses along the wall of the apparatus under the effect of its own weight, causing mixing of the film which is favorable to the transfer of heat and to the transport of the volatiles toward the gas phase. The liquid generally runs from the top downward where, having been purified, it collects. Falling film evaporators generally consist of vertical tubes, optionally grouped into a large number. A device collects the vapors and conveys them to the condenser connected to the vacuum circuit. Several passages over this evaporator, or the combination of several evaporators in series, are sometimes required to achieve a given purity. Flashing with an incondensable gas is possible in these evaporators.

For the scraped film evaporators and in order to increase the mixing efficiency and to work with optionally more viscous products, the film continuously formed on a heated cylinder may be stirred by a rotating system. A rotor provided with scrapers which sweep the entire surface of the cylinder so as to increase the mixing of the film favorable to the transfer of heat and to the transport of volatiles toward the gas phase. The liquid generally runs from the top downward either by the effect of its own weight, or by virtue of the geometry of the scrapers which have an "Archimedean screw" effect causing the film to move downward where, having been purified, it is collected. Flashing with an incondensable gas is possible in these evaporators. Several passages over this evaporator, or the combination of several evaporators in series, are sometimes required to achieve a given purity.

The centrifugal evaporators are based on the same principles; these evaporators are fed with liquid at the center of a rotor consisting of heat exchange plates. The acceleration given to the fluid by the rotating movement of the rotor propels it outward. The vapors released are collected in an appropriate disengaging zone and brought into contact with the condenser linked to the vacuum circuit.

For the continuous flash evaporators, the fluid is continuously fed to a heat exchange type system, for example a jacketed cylindrical heating body. In order to replace the fluid at the heat exchange surface, the heating body is provided with internals, for example static mixers. The hot fluid optionally arrives under pressure in a flash pot under reduced pressure. The volatiles vaporize while the liquids run toward a collector. The vapors are condensed in an exchanger and collected separately.

According to a preferred embodiment of the invention, the reduction of the level of monomers, oligomers and polymers having a molecular mass M<1000 Daltons is performed by extensive devolatilization under a reduced pressure between 3 and 20 mbar and a temperature between 100 and 210° C. until less than 1% of the total molecular distribution has a molecular mass M<1000 Daltons.

The expression "extensive devolatilization" is understood to mean that the devolatilization is maintained until the level of monomers, oligomers and polymers having a molecular mass M<1000 Daltons is less than 1% of the total molecular distribution. For example, for a reduced pressure of about 4 mbar, the "extensive devolatilization" time will be from 3 to 9 h instead of 1 to 2 h for a "standard devolatilization".

According to another preferred embodiment, the polyorganosiloxanes A devoid of toxicity upon skin contact according to the invention are characterized in that they contain, per molecule, at least one siloxyl unit substituted with at least one functional group V directly linked to a silicon atom, said functional group V being a group having one or more steri cally hindered piperidinyl functional groups, chosen from the group consisting of:

a) groups of formula (I):

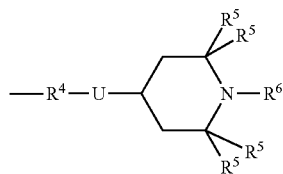

(I)

in which formula:

the radicals $R^5$, which are identical or different, are chosen from linear or branched alkyl radicals having 1 to 3 carbon atoms and the phenyl radical; and the radical $R^6$ represents a hydrogen radical, the radical $R^5$ or the O* atom;

$R^4$ is a divalent hydrocarbon radical chosen from the group consisting of:
- linear or branched alkylene radicals having 2 to 18 carbon atoms;
- alkylene-carbonyl radicals whose linear or branched alkylene part contains 2 to 20 carbon atoms;
- alkylene-cyclohexylene radicals whose linear or branched alkylene part contains 2 to 12 carbon atoms and the cyclohexylene part contains an OH group and optionally 1 or 2 alkyl radicals having 1 to 4 carbon atoms;
- the radicals of formula $R^7$—O—$R^7$ in which the radicals $R^7$, which are identical or different, represent alkylene radicals having 1 to 12 carbon atoms;
- the radicals of formula $R^7$—O—$R^7$ in which the radicals $R^7$ have the meanings indicated above and one of them or both are substituted with one or two —OH groups;
- the radicals of formula $R^7$—COO—$R^7$ in which the radicals $R^7$ have the meanings indicated above; and
- the radicals of formula $R^8$—O—$R^9$—O—CO—$R^8$ in which the radicals $R^8$ and $R^9$, which are identical or different, represent alkylene radicals having 2 to 12 carbon atoms and the radical $R^9$ is optionally substituted with a hydroxyl radical; and U represents —O— or —N($R^{10}$)—, $R^{10}$ being a radical chosen from the group consisting of a hydrogen atom, a linear or branched alkyl radical containing 1 to 6 carbon atoms and a divalent radical of the following formula (II):

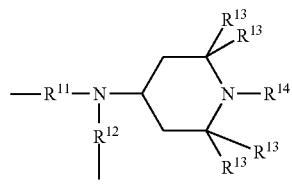

(II)

in which $R^{12}$ has the same meaning as for $R^4$ indicated above, $R^{11}$ represents a linear or branched, divalent alkylene radical having from 1 to 12 carbon atoms, one of the valency bonds (that for $R^{11}$) being linked to the atom of —N$R^{10}$—, the other (that for $R^{12}$) being linked to a silicon atom; the radicals $R^{13}$ are identical or different, chosen from the linear or branched alkyl radicals having 1 to 3 carbon atoms and the phenyl radical; and the radical $R^{14}$ represents a hydrogen radical, the radical $R^{13}$ or the O* atom; and b) groups of formula (III):

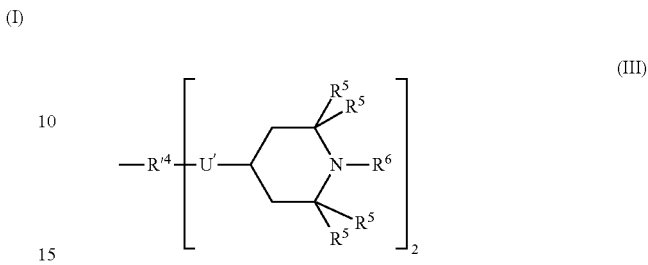

(III)

in which formula:

$R'^4$ is chosen from the group consisting of:
a trivalent radical of the following formula (IV):

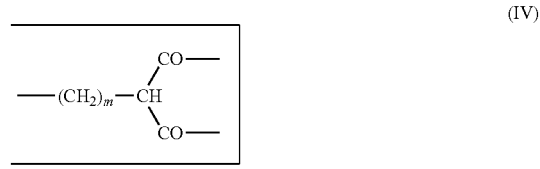

(IV)

where m represents a number from 2 to 20, and a trivalent radical of formula (VI):

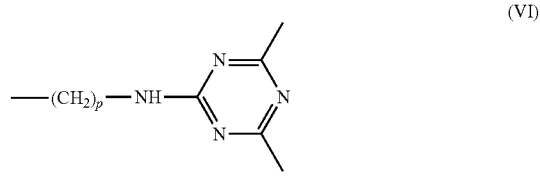

(VI)

where p represents a number from 2 to 20,

U' represents —O— or —N($R^{12}$)—, $R^{12}$ being a radical chosen from the group consisting of a hydrogen atom and a linear or branched alkyl radical containing 1 to 6 carbon atoms; and $R^5$ and $R^6$ have the same meanings as those given in the case of the formula (I);

said polyorganosiloxanes A are characterized in that after their preparations, the level of monomers, oligomers and polymers having a molecular mass M<1000 Daltons is reduced to a value less than 1% relative to the total molecular distribution by means of a technique allowing the selective separation of the monomers, oligomers and polymers having a molecular mass M<1000 Daltons.

The polyorganosiloxanes containing, per molecule, at least one siloxyl unit substituted with at least one functional group V, such as for example a group having one or more sterically hindered piperidinyl functional groups, but with a level of monomers, oligomers and polymers having a molecular mass M<1000 Daltons greater than 1.5% (in general they exhibit a level between 2 and 2.5%) relative to the total molecular distribution, are well known. For example, there may be mentioned those provided by the company Bluestar Silicones under the name RHODORSIL® Huile 21645, Hydrosoft® oil or RHODORSIL® Huile 21650, or those which are prepared according to the procedure described in patent EP-0665258 or in U.S. Pat. No. 5,721,297. There may be mentioned in particular the processes comprising grafting of the functional group V by a hydrosilylation reaction.

Mention is also made of the processes for redistribution or rearrangement from polyorganosiloxanes not comprising the functional group V, and from polyorganosiloxanes comprising functional group groups V linked to silicon atoms. For example, a suitable process for redistribution or rearrangement may comprise the following steps:

1. bringing into contact a polydimethylsiloxane, preferably a cyclic polydimethylsiloxane, hexamethyldisiloxane, and a cyclic polymethylsiloxane comprising functional groups V linked to silicon atoms;
2. heating, introducing a basic catalyst, for example a strong base, and leaving to react; and
3. neutralizing, for example with the aid of weak acid, and then isolating the polyorganosiloxanes comprising the functional groups V for example by means of a standard devolatilization; cooling and withdrawing.

These polyorganosiloxanes may constitute an excellent raw material for preparing the polyorganosiloxanes A devoid of toxicity upon skin contact according to the invention. Accordingly, these polyorganosiloxanes are treated according to the invention so as to provide the polyorganosiloxanes A devoid of toxicity upon skin contact according to the invention. These amino silicones having sterically hindered groups may be provided in the form of solutions, dispersions, microemulsions or emulsions.

Advantageously, the polyorganosiloxanes A are composed of siloxyl units represented by the following formula (VIII):

$$[(Z)(R^{15})_2SiO_{1/2}]_{2+w}[(R^{16})_2SiO_{2/2}]_x[(Z)(R^{17})SiO_{1/2}]_y \\ [(Z)SiO_{3/2}]_w \quad (VIII)$$

in which formula:
(1) the symbols Z, which are identical or different, represent $R^{15}$ or a functional group V:
(2) the symbols $R^{15}$, $R^{16}$ and $R^{17}$, which are identical or different, each represent an optionally substituted, linear or branched $C_1$-$C_{12}$ alkyl radical, an optionally substituted $C_5$-$C_{10}$ cycloalkyl radical, an optionally substituted $C_6$-$C_{18}$ aryl radical, an optionally substituted aralkyl radical or a radical —$OR^{18}$ where $R^{18}$ represents a hydrogen, a linear, branched or cyclic alkyl radical having from 1 to 15 carbon atoms or a hydrocarbon group comprising an epoxide and/or polyether functional group;
(3) the functional groups V have the same definition as above (=group having one or more sterically hindered piperidinyl functional groups); and
(4)—the number of siloxyl units with no functional group V is between 1 and 800,
the number of siloxyl units with a functional group V is between 1 and 50, and
$0 \leq w < 50$ and $8 \leq y < 798$.

According to another preferred embodiment, the polyorganosiloxanes A of formula (VIII) are linear (w=0) and the symbols $R^{15}$, $R^{16}$ and $R^{17}$ of formula (VIII) are methyl groups.

According to a particularly preferred embodiment, the polyorganosiloxanes A according to the invention are compounds of the following general formula (IX):

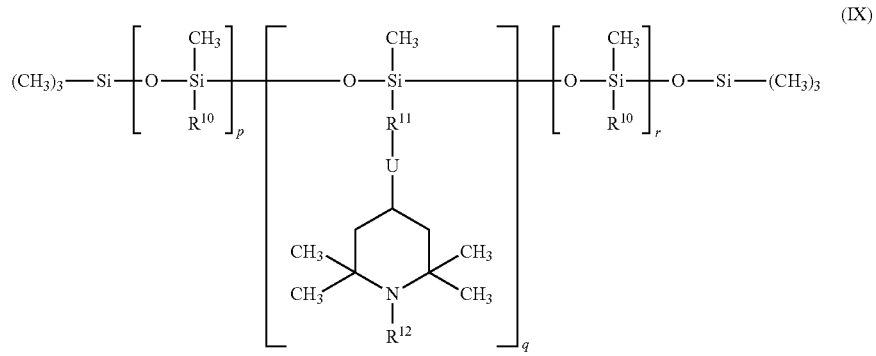

in which formula:
the various units are randomly distributed in the chain;
p represents a number greater than or equal to 0 and preferably between 1 and 2000;
r represents a number greater than or equal to 0 and preferably between 1 and 2000;
q represents a number greater than or equal to 1, preferably between 1 and 50;
$R^{10}$ represents a linear or branched alkyl radical having 1 to 18 carbon atoms;
the group U has the same meaning as U' and $R^{11}$ has the same meaning as $R'^4$ and $R^{12}$ has the same meaning as $R^6$ described above.

According to a preferred embodiment, the sum p+r is between 1 and 800.

According to another preferred embodiment, the functional group V is a propyloxytetramethylpiperidine radical of the following formula (X):

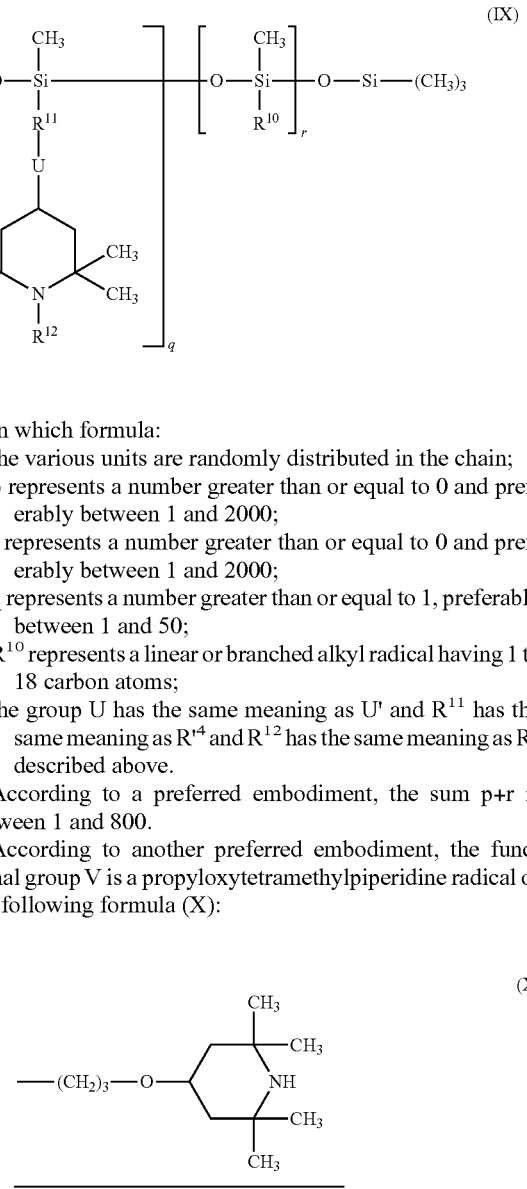

The polyorganosiloxanes A devoid of toxicity upon skin contact in which 0.8 to 4% of the silicon atoms are substituted by a functional group V according to the invention are particularly advantageous, especially when they are used in cosmetic compositions as described below.

According to another particularly preferred embodiment, the functional group V is present in an amount of 2 to 4% by weight relative to the total weight of the silicone oil.

Another subject of the invention relates to a cosmetic and/or dermatological composition devoid of toxicity upon skin contact, characterized in that it comprises, in a cosmetically acceptable medium, at least one polyorganosiloxane A according to the invention and as described above.

The compositions according to the invention contain a cosmetically acceptable aqueous medium. They have a pH which may range from 3.5 to 11, preferably from 5.5 to 11 and more preferably still from 5.5 to 8.5.

The "cosmetically acceptable medium" (or "cosmetically acceptable vector") for the compositions according to the invention more particularly consists of water and optionally of cosmetically acceptable organic solvents.

"Cosmetically Acceptable Medium" or "Cosmetically Acceptable Vector":

It is possible to use any cosmetically acceptable medium which makes it possible to formulate the polyorganosiloxanes A according to the invention, and to obtain the form of cosmetic composition desired, for the intended use. Various cosmetically acceptable media for various types of formulation are known to a person skilled in the art.

By way of examples of cosmetically acceptable vectors, there may be mentioned aqueous vectors (comprising water), alcoholic vectors (comprising an alcohol, for example ethanol, isopropanol, ethylene glycol and polyethylene glycol), propylene glycol, aqueous-alcoholic vectors (comprising a mixture of water and an alcohol, for example ethanol, isopropanol, ethylene glycol or polyethylene glycol). Some volatile or nonvolatile oils may also be used. Mention is made for example of fluid silicones, such as cyclopentasiloxane, for example Mirasil CM5 marketed by Bluestar Silicones.

Persons skilled in the art know how to choose the vectors suitable for the desired types of formulations, and for their intended usage. For example, aqueous vectors are generally used for shampoos or shower gels. A propylene glycol vector may be used compositions in the form of creams. A cyclomethicone vector may be used for makeup compositions, for example for foundations.

Surfactants:

The composition may comprise at least one surfactant. This may be a mixture of various surfactants. It is preferably at least one anionic surfactant, alone or as a mixture. The surfactant may additionally comprise anionic surfactants, amphoteric (zwitterionic or true amphoteric) surfactants, neutral surfactants and/or cationic surfactants, alone or as a mixture. The compositions comprising at least one amphoteric surfactant and optionally one anionic surfactant are particularly advantageous, in particular for reasons of smoothness. The total amount of surfactant in the composition may be between 5 and 30% by weight.

For compositions intended for treating the hair, such as shampoos, the amount of surfactant is advantageously between 10 and 20% by weight. Such compositions may comprise salts, for example sodium or ammonium chloride, advantageously in an amount of less than 3% by weight.

For compositions intended for the treatment of the skin, such as shower gels, the amount of surfactant is advantageously between 5 and 15% by weight. Such compositions preferably also comprise at least 2% by weight of salts, for example of sodium or ammonium chloride.

The proportion by weight of anionic surfactant relative to all the surfactants is preferably greater than 50%, preferably greater than 70%.

The anionic surfactants may be chosen from the following surfactants:

alkyl ester sulfonates, for example of formula R—CH(SO$_3$M)-CH$_2$COOR', or alkyl ester sulfates, for example of formula R—CH(OSO$_3$M)-CH$_2$COOR', where R represents a $C_8$-$C_{20}$, preferably $C_{10}$-$C_{16}$, alkyl radical, R' a $C_1$-$C_6$, preferably a $C_1$-$C_3$, alkyl radical and M an alkaline-earth cation, for example sodium, or the ammonium cation. Mention may be made most particularly of methyl ester sulfonates in which the radical R is $C_{14}$-$C_{16}$;

alkyl benzenesulfonates, more particularly as $C_9$-$C_{20}$, primary or secondary alkyl sulfonates, in particular as $C_8$-$C_{22}$, alkylglycerol sulfonates;

alkyl sulfates, for example of formula ROSO$_3$M, where R represents a $C_{10}$-$C_{24}$, preferably $C_{12}$-$C_{20}$, alkyl or hydroxyalkyl radical; M a cation with the same definition as above;

alkyl ether sulfates, for example of formula RO(OA)$_n$SO$_3$M, where R represents a $C_{10}$-$C_{24}$, preferably $C_{12}$-$C_{20}$ alkyl or hydroxyalkyl radical; OA representing an ethoxylated and/or propoxylated group; M representing a cation with the same definition as above, n generally ranging from 1 to 4, such as for example lauryl ether sulfate with n=2;

alkyl amide sulfates, for example of formula RCONHR'OSO$_3$M, where R represents a $C_2$-$C_{22}$, preferably $C_6$-$C_{20}$, alkyl radical, R' a $C_2$-$C_3$ alkyl radical, M representing a cation with the same definition as above and their polyalkoxylated (ethoxylated and/or propoxylated) derivatives (alkyl amidoether sulfates)

salts of saturated or unsaturated fatty acids, for example such as those in the form of $C_8$-$C_{24}$, preferably $C_{14}$-$C_{20}$, and of an alkaline-earth cation, N-acyl N-alkyltaurates, alkyl isethionates, alkyl succinamates and alkyl sulfosuccinates, monoesters or diesters of sulfosuccinates, N-acyl-sarcosinates, polyethoxycarboxylates phosphate mono- and diesters, for example of the following formula:

(RO)$_x$—P(=O)(OM)$_{x'}$ or R represents an optionally polyalkoxylated alkyl, alkylaryl, arylalkyl or aryl radical, x and x' being equal to 1 or 2, provided that the sum of x and x' is equal to 3, M representing an alkaline-earth cation.

The nonionic surfactants may be chosen from the following surfactants:

alkoxylated fatty alcohols;
alkoxylated triglycerides;
alkoxylated fatty acids;
alkoxylated sorbitan esters;
alkoxylated fatty amines;
alkoxylated di(phenyl-1-ethyl)phenols;
alkoxylated tri(phenyl-1-ethyl)phenols;
alkoxylated alkylphenols;
the products resulting from the condensation of ethylene oxide with a hydrophobic compound resulting from the condensation of propylene oxide with propylene glycol, such as Pluronic marketed by BASF;
the products resulting from the condensation of ethylene oxide, the compound resulting from the condensation of propylene oxide with ethylene-diamine, such as Tetronic marketed by BASF;
alkyl polyglycosides such as those described in U.S. Pat. No. 4,565,647; and
fatty acid amides, for example as $C_8$-$C_{20}$.

The amphoteric surfactants (true amphoteric surfactants comprising an ionic group and a potentially ionic group of opposite charge, or zwitterionic surfactants simultaneously comprising two opposite charges) may be chosen from the following surfactants:

betaines in general, in particular carboxybetaines of for example laurylbetaine (Mirataine BB from the company Rhodia) or octylbetaine; amidoalkylbetaines such as cocamidopropylbetaine (CAPB) (Mirataine BDJ from the company Rhodia Chimie);

sulfobetaines or sultaines such as cocamidopropylhydroxysultaine (Mirataine CBS from the company Rhodia);

alkyl amphoacetates and alkyl amphodiacetates, such as for example comprising a coco or lauryl chain (Miranol C2M, C32, L32 in particular, from the company Rhodia);

alkyl amphopropionates or alkyl amphodipropionates (Miranol C2M SF); and alkyl amphohydroxypropylsultaines (Miranol CS).

The cationic surfactants may be chosen from the salts of optionally polyethoxylated primary, secondary or tertiary fatty amines, quaternary ammonium salts such as tetraalkylammonium, alkylamidoalkylammonium, trialkylbenzylammonium, trialkylhydroxyalkylammonium or alkylpyridinium chlorides or bromides, imidazoline derivatives, amine oxides with a cationic character.

Stabilizing and/or Conditioning and/or Conditioning Aid Agent

The cosmetic composition according to the invention may advantageously comprise at least one stabilizing and/or conditioning (conditioning agents) and/or conditioning aid agent. The expression suspending agents is also sometimes used. The expression conditioning aid is understood to mean that the presence of the agent improves the conditioning linked to other compounds, for example oils or silicones. The agents are understood to mean agents different from the polyorganosiloxane of formula (I). Such agents are known to a person skilled in the art. The composition according to the invention may comprise several of these agents (mixtures or combinations), in order to combine their effects and/or create synergies. Moreover, some agents may perform several functions. That is the case for example for polysaccharides, and their cationic derivatives, for example guar cationic derivatives.

The proportion by weight of such agents may be typically from 0.1% to 10% by weight, preferably from 0.3% to 8% by weight, for polysaccharides and other agents.

By way of examples of stabilizing agents, there may be mentioned:

crosslinked polyacrylates, for example polymers of the CARBOPOL or CARBOMER type marketed by BF Goodrich or Noveon, ACRITAMER marketed by RITA or TEGO CARBOMER marketed by Goldschmidt. These compounds may be typically present in a quantity of 0.1 to 3%, preferably 0.3 to 2%, by weight relative to the composition;

acrylates/aminoacrylates/$C_{10}$-$C_{30}$ alkyl PEG 20 itaconate copolymers marketed by National Starch under the name STRUCTURE PLUS. These compounds may be typically present in a quantity of 0.1 to 3%, preferably 0.3 to 2%, by weight relative to the composition; and insoluble solids forming a network in the composition. These may be fatty acid mono- and/or diesters of ethylene glycol, the fatty acids being preferably $C_{16}$-$C_{18}$. They may be in particular ethylene glycol distearate (EGDS), for example marketed by Rhodia as a concentrate with other ingredients under the name MIRASHEEN. This compound may be typically present in a quantity of 3 to 10%, preferably 5 to 8% by weight relative to the composition.

There may also be mentioned viscosity-promoting, gelling or texturing agents such as anionic acrylic copolymers of the ACULYNE type marketed by ISP or Rohm & Haas, polysaccharides and their noncationic derivatives such as cellulose derivatives such as hydroxypropylcellulose, carboxymethylcellulose, guar nonionic derivatives such as hydroxypropylguar (for example Jaguar HP marketed by Rhodia), carob, tara or cassia gum, xanthan gum (for example Rhodicare marketed by Rhodia), succinoglycans (for example Rheozan marketed by Rhodia), alginates, carrageenans, chitin derivatives or any other polysaccharide having a texturing function. These polysaccharides and their derivatives may be incorporated, alone or as a synergistic combination, into other polysaccharides. These compounds may be typically present in a quantity of 0.1 to 3%, preferably 0.3 to 1% by weight relative to the composition.

By way of examples of stabilizing agents and/or conditioning and/or conditioning aid agents, there may be mentioned:

cationic polymers derived from polysaccharides, for example cationic cellulose derivatives, cationic starch derivatives, cationic guar derivatives, cationic carob derivatives;

synthetic cationic polymers; and mixtures or combinations of these agents.

The synthetic or nonsynthetic cationic polymers, which can provide a function of conditioning agent, are in particular polymers of the polyquaternium type, such as for example polyquaternium-1, polyquaternium-2, polyquaternium-4, polyquaternium-5, polyquaternium-6 (also known as Merquat 1000 available from Nalco), polyquaternium-7 (also known as Merquat 5500 available from Nalco), polyquaternium-8, polyquaternium-9, polyquaternium-10 (also known as Polymer JR 400, marketed by Amerchol), polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-22 (also known as Merquat 280, 281, 298 available from Nalco), polyquaternium-24, polyquaternium-27, polyquaternium-28, polyquaternium-29 (also known as Kytamer KCO available from Amerchol), polyquaternium-30, polyquaternium-31, polyquaternium-32, polyquaternium-33, polyquaternium-34, polyquaternium-35, polyquaternium-36, polyquaternium-37, polyquaternium-39 (also known as Merquat 3300, 3331 available from Nalco), polyquaternium-44, polyquaternium-27 (also known as Merquat 2001 available from Nalco) and polyquaternium-55.

The cationic guar derivatives may have a function of agent for stabilizing the formulations, of conditioning agent and/or of conditioning aid agent. By way of examples, there may be mentioned:

guar hydroxypropyltrimonium chloride (Jaguar C 13S, Jaguar C14S, Jaguar C17, Jaguar Excel, Jaguar C 2000, marketed by Rhodia);

hydroxypropyl guar hydroxypropyltrimonium chloride (Jaguar C162, marketed by Rhodia);

cellulose poly(oxy-1,2-ethanediyl)-2-hydroxy-3-trimethylammonium-propyl ether chloride or polyquaternium-10.

Other Polyorganosiloxane:

The composition according to the invention may comprise a polyorganosiloxane different from the polyorganosiloxanes A. This other polyorganosiloxane may be present for example in the form of an emulsion, defining in the cosmetically acceptable vector a second family of droplets (the expression co-emulsions is often used). It may also be in the form of a mixture with the polyorganosiloxanes A in the form of an emulsion of droplets of the mixture (the expression emulsions of mixtures may be used), or in the form of droplets dispersed in the polyorganosiloxanes A (the expression multiple emulsions may be used).

The polyorganosiloxane different from the polyorganosiloxanes A may be a polyorganosiloxane comprising polar groups, or a nonpolar polyorganosiloxane.

By way of examples of polyorganosiloxanes comprising polar groups, there may be mentioned: dimethiconols, amodimethicones, trimethylsilyl amodimethicone, dimethicone copolyols, ternary copolyols, Silatrizole, dimethicone copolyol amine, silicone quaternium (CTFA silicone quaternium 1 to 10).

By way of examples of nonpolar polyorganosiloxanes, there may be mentioned polydimethylorganosiloxanes (PDMS or dimethicone), silicones having phenyl groups, silsesquioxane (structure "T") & silicates (structure "Q"), crosslinked silicones, copolymers comprising silicone groups, silicone resins, silicone waxes and volatile alkyl methyl siloxanes.

Just as for polyorganosiloxanes A, the emulsions of polyorganosiloxane different from the polyorganosiloxanes A may be prepared by emulsification in situ or by prior emulsification, and have droplet sizes of less than 0.15 µm, or between 0.15 µm and 2 µm, or greater than or equal to 2 µm. Reference may be made to the passage on emulsions below.

UV Screening Agents

The composition according to the invention may comprise UV screening agents. These may be organic or inorganic agents. They may be for example inorganic agents such as dispersions of particles based on titanium dioxide, zinc oxide or cerium oxide, preferably in nano-particulate form, where appropriate coated with a layer based on an oxide or hydroxide of silica or aluminum, for example, the dispersion marketed under the name Mirasun® TiW60 from Rhodia. They may also be organic molecules. Such molecules are known to a person skilled in the art. By way of examples of organic molecules, mention may be made of the following compounds: Eusolex OCR or Eusolex 6300 (Merck); Parsol 1789, Parsol HS, or Parsol MCX (Givaudan Roure); Mexoril SX (Chimex); Escalol 567, Escalol 587, or Escalol 507 (ISP/Van Dyk); Uvinul MS-40, Uvinul T-150, or Spectrasorb UV-24 (BASF); Neo Heliopan MA or Neo Heliopan Type E 1000 (Haarmann & Reimer): Tinosorb M (Ciba), Homomenthyl salicylate.

Other Ingredients:

As other ingredients which may be included in the composition, there may be mentioned coloring agents, dyes or colorants, fragrances, perfumes, fragrance-masking agents, polymers, buffering agents, complexing agents, complexing capsules, soluble salts, for example salts of alkali metals, alkaline-earth metals or ammonium, for example, NaCl or $NaSO_4$ or $NH_4Cl$, Lewis acids, particulate thickeners, polymeric thickeners, thickening waxes, oils, emollients, humectants, moisturizing agents, pearlescent agents, opacifiers, dispersing agents, agents promoting the suspension of particles, antimicrobial agents, preservatives, proteins, plant extracts, oxidizing agents, viscosity-modifying agents, gelling agents, chelators, reducing agents.

The composition may additionally comprise a large variety of hydrophilic or nonhydrophilic active agents. These may be antifungal agents, antibacterial agents, for example triclosan, antidandruff agents, for example zinc-pyrithione, antiaging agents, anticellulite agents.

By way of examples of active substances which can be used in the cosmetics field, there may be mentioned vitamins, such as vitamin A and its derivatives, in particular its esters such as the acetate, palmitate, propionate, vitamin B2, pantothenic acid, vitamin D and vitamin E; mono-, di- and triglycerides; bactericides; UV absorbers, such as the aminobenzoate derivatives of the PABA and PARA type, salicylates, cinnamates, anthranilates, dibenzoylmethanes, camphor derivatives and mixtures thereof.

Antiaging agents may likewise be used. By way of examples of such agents, there may be mentioned in particular retinoids, fat-soluble vitamins, derivatives of vitamin C such as the esters, in particular the acetate, propionate, palmitate; ceramides, pseudo-ceramides, phospholipids, fatty acids, fatty alcohols, cholesterol, sterols and mixtures thereof. As preferred fatty acids and alcohols, there may be mentioned more particularly those having linear or branched alkyl chains containing from 12 to 20 carbon atoms. These may include in particular linoleic acid.

It is likewise possible to use anticellulite agents, such as in particular isobutylmethylxanthine and theophyline; as well as antiacne agents, such as for example resorcinol, resorcinol acetate, benzoyl peroxide and numerous natural compounds.

Flavorings, perfumes, essential oils, essences, may also be used as active substance. By way of example, there may be mentioned the oils and/or essences of mint, spearmint, peppermint, menthol, vanilla, cinnamon, bay, anise, eucalyptus, thyme, sage, cedar leaf, nutmeg, citrus (lemon, lime, grapefruit, orange), fruits (apple, pear, peach, cherry, plum, strawberry, raspberry, apricot, pineapple, grapes, and the like), alone or as mixtures. It is also possible to use compounds such as benzaldehyde, isoamyl acetate, ethyl butyrate and the like.

The antimicrobial agents may be chosen from thymol, menthol, triclosan, 4-hexylresorcinol, phenol, eucalyptol, benzoic acid, benzoic peroxide, butylparaben, and mixtures thereof.

The cosmetic compositions may also contain polymers exhibiting film-forming properties which may be used to provide a fixing function. These polymers are generally present at concentrations between 0.01 and 10%, preferably between 0.5 and 5%. They are preferably of the polyvinylpyrrolidone type, polyvinylpyrrolidone and methyl methacrylate copolymers, polyvinylpyrrolidone and vinyl acetate copolymers, ethylene glycol polyterephthalate/polyethylene glycol copolymers, sulfonated terephthalic copolyester polymers.

It is also possible to incorporate moisturizing agents into the cosmetic compositions. By way of illustration of the latter, mention may be made in particular of glycerol, propylene glycol, urea, collagen, gelatin, and emollients which are generally chosen from alkyl monoglycerides, alkyl diglycerides, triglycerides such as oils extracted from plants or their hydrogenated derivatives, mineral oils or paraffin oils, diols, fatty esters, silicones (see above).

Preservatives, such as the p-hydroxybenzoic acid esters, sodium benzoate, or any chemical agent which avoids bacterial proliferation or the proliferation of molds and traditionally used in cosmetic compositions are generally introduced into these compositions in an amount of 0.01 to 3% by weight. Preservatives are for example marketed under the names Glydant, Germaben, Kathon.

Physicochemical Form of the Cosmetic Composition:

The cosmetic composition comprises a cosmetically acceptable vector and the polyorganosiloxanes A according to the invention. The polyorganosiloxanes dispersed in the cosmetically acceptable vector, or in a mixture of ingredients comprising the cosmetically acceptable vector. The dispersion may be for example:

a solution of the polyorganosiloxanes A according to the invention in the cosmetically acceptable vector or in a mixture comprising the cosmetically acceptable vector;

a stable emulsion of droplets comprising the polyorganosiloxanes A according to the invention in the cosmetically acceptable vector, or a combination of phases separated into at least one stratum comprising the cosmetically acceptable vector, and one stratum comprising the polyorganosiloxanes A according to the invention, which may form a dispersion of droplets comprising the polyorganosiloxanes A according to the invention in the cosmetically acceptable vector after stirring by the user.

Of course, the cosmetically acceptable vector may comprise other ingredients than the polyorganosiloxanes A according to the invention, it being possible for these other ingredients to be present in a solution or in a dispersion, for example in the form of a suspension of solid particles, or of an emulsion defining a family of droplets.

Likewise, the polyorganosiloxanes A according to the invention may define a phase in which one or more other ingredients are dispersed.

Some characteristics of cosmetic compositions according to the invention in the form of emulsions are detailed below.

Emulsions:

The cosmetic compositions according to the invention may be in the form of emulsions of droplets comprising the polyorganosiloxanes A according to the invention dispersed in the cosmetically acceptable vector, preferably in an aqueous vector.

The droplets of the emulsion may be large in size to a lesser or greater degree. Reference may thus be made to microemulsions, miniemulsions or macroemulsions. In the present application, the term "emulsion" covers in particular all these types of emulsions. Without wishing to be bound by any theory, it is specified that microemulsions are generally thermodynamically stable systems, generally comprising large quantities of emulsifying agents. The other emulsions are generally systems in a nonthermodynamically stable state, which preserve for a certain period, in a metastable state, the mechanical energy provided during the emulsification. These systems generally comprise smaller quantities of emulsifying agents.

The compositions in the form of emulsions may be obtained by mixing the vector, preferably an aqueous vector, the polyorganosiloxanes A according to the invention, and in general an emulsifying agent, and then emulsifying. This may be described as emulsification in situ.

The compositions in the form of an emulsion may also be obtained by mixing the vector, preferably an aqueous vector, with a previously prepared emulsion of droplets comprising the polyorganosiloxanes A according to the invention in an external phase, preferably miscible with the cosmetically acceptable vector, preferably of the same type as said vector, preferably an aqueous vector. This embodiment may be preferred because it is simple to carry out. In addition, this embodiment is particularly suitable for using cosmetic compositions in which the polyorganosiloxane of formula (I) is in the form of a microemulsion. This may be described as a preliminary emulsification.

According to a particular embodiment, the emulsion is a microemulsion, in which the size of the droplets is less than 0.15 µm. In this embodiment, the composition preferably comprises a proportion greater than 10% by weight, preferably of at least 15% by weight of emulsifying agent relative to the weight of the polyorganosiloxanes A.

The size of the droplets of microemulsion may be measured on an emulsion prepared prior to its introduction into the cosmetic composition, by dynamic light scattering (DQEL), for example as described below. The apparatus used for example consists of a Spectra-Physics 2020 laser, a Brookhaven 2030 correlator and the associated computing. As the sample is concentrated, it is diluted in deionized water and filtered on 0.22 µm, so as to finally be at 2% by weight. The diameter obtained is an apparent diameter. The measurements are performed at an angle of 90° and 135°. For the measurements of size, in addition to the conventional analysis by cumulants, three versions of the self-correlation function are used (exponential sampling or EXPSAM described by Pr. Pike, the "Non Negatively Constrained Least Squares" or NNLS method and the CONTIN method described by Pr. Provencher), which each give a size distribution weighted by the scattered intensity, and not by the mass or the number.

The refractive index and the viscosity of the water are taken into account.

According to an advantageous embodiment, the microemulsion is transparent. The microemulsion may for example exhibit a transmittance of at least 90%, preferably of at least 95%, at a wavelength of 600 nm, measured for example with the aid of a Lambda 40 UV-Vis spectrometer at a concentration of 0.5% by weight in water. In this context, the cosmetic composition may be advantageously transparent. It may for example exhibit a transmittance of at least 90%, preferably of at least 95%, at a wavelength of 600 nm, measured for example with the aid of a Lambda 40 UV-Vis spectrometer.

According to another particular embodiment, the emulsion is an emulsion whose mean droplet size is greater than or equal to 0.15 µm, for example greater than 0.5 µm, or than 1 µm, or than 2 µm, or than 10 µm, or than 20 µm, and preferably less than 100 µm. The size of the droplets may be measured on an emulsion prepared prior to its introduction into the cosmetic composition, or directly on the cosmetic composition diluted in water, by optical microscopy and/or laser granulometry (Horiba LA-910 laser scattering analyzer). In this embodiment, the composition preferably comprises a proportion of less than 10% by weight of emulsifying agent, relative to the weight of the polyorganosiloxanes A according to the invention.

As mentioned above, the droplets of the emulsion may comprise other ingredients than the polyorganosiloxanes A according to the invention. Accordingly, the polyorganosiloxanes A according to the invention may be mixed with a miscible ingredient, for example, an oil, preferably a silicone oil, the mixture forming the emulsion. The droplets of the polyorganosiloxanes A according to the invention may also comprise an emulsion of smaller droplets of an immiscible phase (inner phase). The emulsion is then a multiple emulsion comprising an inner phase dispersed in an intermediate phase comprising the polyorganosiloxanes A according to the invention, itself dispersed in the vector. The ingredients which may be contained in the inner phase may be for example active ingredients offering a positive effect on the skin and/or the hair. This may also include agents promoting the deposition of the polyorganosiloxanes A according to the invention, or other ingredients, on the skin and/or the hair.

Emulsifying Agents:

Emulsifying agents are agents which can make it possible to obtain an emulsion of the polyorganosiloxanes A according to the invention in the vector, preferably water. They may be for example:

a nonionic surfactant, a nonionic amphiphilic polymer, optionally combined with one or more anionic surfactants and/or anionic amphiphilic polymers, a particulate surfactant optionally combined with a cosurfactant, or a protective colloid.

Particulate Surfactant:

According to a particular embodiment, the emulsifying agent is a particulate surfactant optionally combined with a cosurfactant.

The particulate surfactant is preferably chosen from solid particulate compounds, whose angle of contact is close to 0°, combined with at least one costabilizer chosen from nonionic, anionic, cationic or zwitterionic surfactants.

The particulate surfactant is for example a precipitated silica, a colloidal silica, a silicoaluminate, zinc oxide, titanium oxide, or a mixture of these compounds, these compounds comprising, where appropriate, a surface treatment.

Protective Colloid:

According to another particular embodiment, the emulsifying agent is a protective colloid. It may be for example a polyvinyl alcohol, where appropriate partially hydrolyzed.

The protective colloid content is advantageously from 3 to 30% by dry weight relative to the inner emulsion, preferably from 5 to 25%.

Nonionic Surfactant

According to another particular embodiment, the emulsifying agent comprises a nonionic surfactant. This is preferably a polyalkoxylated nonionic surfactant, for example chosen from the group consisting of:

alkoxylated fatty alcohols;
alkoxylated triglycerides;
alkoxylated fatty acids;
alkoxylated sorbitan esters;
alkoxylated fatty amines;
alkoxylated di(1-phenylethyl)phenols;
alkoxylated tri(1-phenylethyl)phenols; and
alkoxylated alkylphenols:

where the number of alkoxy units, more particularly oxyethylene and/or oxypropylene, is such that the HLB value is greater than or equal to 10.

Nonionic Amphiphilic Polymer

According to another particular embodiment, the external emulsifying agent comprises a nonionic amphiphilic polymer. This polymer may be combined with one or more anionic surfactants and/or anionic amphiphilic polymers.

By way of nonionic amphiphilic polymers, there may be mentioned the triblock copolymers (polyethylene glycol)-(polypropylene glycol)-(polyethylene glycol).

As regards the nonionic or anionic amphiphilic polymers, use may be made of a polymer comprising at least two blocks, one of them being hydrophilic, the other hydrophobic. Comb copolymers may be used.

Said amphiphilic polymers may be advantageously obtained by the so-called living or controlled free-radical polymerization. By way of nonlimiting examples of processes for the so-called living or controlled polymerization, reference may be made in particular to applications WO 98/58974, WO 00/75207 and WO 01/42312 (xanthate), WO 98/01478 (dithioesters), WO 99/03894 (nitroxides); WO 99/31144 (dithiocarbamates), WO 02/26836 (dithiocarbazates); WO 02/10223 (dithiophosphoroesters), WO 96/30421 (atom transfer free-radical polymerization—ATRP). Amphiphilic polymers may also be obtained by anionic polymerization. They may likewise be prepared using (in particular anionic) ring opening polymerizations, or by chemical modification of the polymer.

More particularly, as regards the nonionic amphiphilic polymer, preferably polyoxyalkylenated, present in the external aqueous phase, it may be chosen from polymers that are at least partially miscible in the external aqueous phase and preferably from the polyethylene glycol-polypropylene glycol-polyethylene glycol triblock copolymers. It is specified that polymers of the polyvinyl alcohol or polyacrylic acid/polybutyl acrylate/polyacrylic acid triblock type may be used for this purpose.

Type of Formulation of the Composition and Uses:

The composition according to the invention may be formulated in various forms, depending on the appearance which it is desired to confer on it, the sensory properties (viscosity, feel, permanence and the like) which it is desired to confer on it, and of course the use which it is desired to make of it. The various types of formulation and the various uses are modulated by the nature and quantity of the ingredients present in the composition, and are known to a person skilled in the art.

Accordingly, the composition may be formulated in the form of gels, fluids that are viscous to a greater or lesser degree, milks, creams, oils, sprays, mousses, gel sticks, pastes, lotions, dye concentrates, and the like.

The compositions may be chosen in particular from the compositions listed in table I below, with physicochemical forms of the polyorganosiloxanes A, types of formulation and uses also listed in table (I) below. For these compositions, physicochemical forms, type of formulations and uses, reference may be made to more detailed parts of the present application.

TABLE I

| Composition | Physicochemical form: silicones A according to the invention | Type of formulation | Use |
|---|---|---|---|
| Shampoos | Emulsion | Fluid | Cleansing and/or care of the hair and/or temporary dyeing and/or fixing of the coloration, with rinsing |
| Conditioner | Emulsion | Fluid | Haircare, and/or disentanglement and/or hairstyling aid and/or temporary dyeing and/or fixing of the coloration and/or conditioning and/or conditioning after dyeing, with or without rinsing |
| Shower gel | Emulsion | Fluid or gel | Cleansing and/or care of the skin |
| Hair mask | Emulsion | Very viscous fluid | Haircare |
| Antisun cream | Emulsion | Cream | Protection of the skin against UV radiation |
| Antisun milk | Emulsion | Milk | Protection of the skin against UV radiation |
| Antisun oil | Inverse emulsion or solution | Oil | Protection of the skin against UV radiation |
| Antisun spray | Emulsion | Fluid | Protection of the skin against UV radiation |
| Care cream | Emulsion | Cream | Skincare |

TABLE I-continued

| Composition | Physicochemical form: silicones A according to the invention | Type of formulation | Use |
|---|---|---|---|
| Makeup remover | Emulsion | Cream or fluid or gel | Care and/or cleansing of the skin and/or of the eyelashes |
| Makeup | Emulsion, or inverse suspension or solution | Cream, fluid, mascara, powder, gels, sticks | Coloration of the skin or the eyelashes |
| Deodorant | Emulsion or inverse emulsion | Aerosol, gel, sticks, substance which may be applied with the aid of a ball applicator | Reducing the effects of perspiration, applied to the skin |
| Shaving foam | Emulsion | Very fluid liquid or gel forming a foam after aerosol spraying | Preparation for shaving |
| Hairstyling or fixing spray | Emulsion | Fluid | Hair shaping |
| Hairstyling or fixing gel | Emulsion | Gel | Hair shaping |
| Hairstyling or fixing mousse | Emulsion | Very fluid liquid or gel forming a mousse after aerosol spraying | Hair shaping |
| Dye composition | Emulsion | Gel or viscous liquid | Permanent or semipermanent dyeing |

Among the uses of the compositions, mention may be made of the uses in which the composition is intended to be rinsed off and the uses in which the composition is intended not to be rinsed off.

Compositions Intended to be Rinsed Off

According to advantageous embodiments, the composition is a care composition for the skin and/or the hair, preferably for cleansing and/or treating the skin and/or the hair, said composition being in the form of a fluid. It is advantageously a shower gel, a shampoo, a conditioner intended to be rinsed off, a skin or hair mask, intended to be rinsed off after use.

For shower gels and shampoos, the composition may advantageously comprise:

at least one anionic and/or amphoteric surfactant, alone or as a mixture, optionally at least one stabilizer and/or conditioner and/or conditioning aid, or a mixture of such agents, optionally another polyorganosiloxane, mixtures of these ingredients.

Such ingredients have been described above.

For the conditioners intended to be rinsed off, the composition may be advantageously a fairly viscous formulation, for example a cream, in the form of an emulsion comprising an aqueous phase in which a texturing oily emulsified phase and emulsified droplets of the polyorganosiloxanes A according to the invention are dispersed. The aqueous phase advantageously comprises a conditioner, for example a cationic polymer. Such polymers were described above. The aqueous phase may also advantageously comprise a cationic surfactant. Such surfactants were described above. This may include for example stearylbenzyldimethylammonium chloride, cetyltrimethylammonium chloride (cetrimonium chloride), distearyldimethylammonium chloride or stearamidopropyldimethylamine, for example in a quantity of 0.3 to 2% by weight.

Compositions Intended not to be Rinsed Off ("Leave-On"):

According to advantageous embodiments, the composition is a composition for skin and/or hair care, in the form of a fluid or in another form, preferably for treating and/or protecting and/or modifying the appearance of the skin and/or the hair, intended to be left on the skin and/or the hair after application.

This may include for example a conditioner intended not to be rinsed off, a disentangling milk, a disentangling lotion, a smoothing lotion, a cuticle coat, a hair-styling care product, a hair-styling and restyling care product, a sun protection product (antisun cream, antisun milk, antisun oil), a care cream, a makeup remover, a makeup, makeup-removing or moisturizing wipes, shaving foams, hairstyling or fixing mousses, hairstyling or fixing gels.

Shower gels, shampoos or conditioners intended to be rinsed off or not, comprising the polyorganosiloxanes A according to the invention may thus present improvements in terms of:

fixing of the colorations obtained before or during the application of the composition, conditioning of the hair, particularly on damaged hair and/or on the ends, conditioning of the skin, varying of the conditioning of the hair and/or the skin (mild or strong conditioning)

varying of the conditioning of the hair and/or the skin according to the level of nitrogen present in the polyorganosiloxane, cosmetic effects such as the softness, suppleness, disentanglement, gloss, hair-styling ability on dry or wet hair, low yellowing, repair of damage linked to sunlight, decoloring linked to sunlight or other external conditions, or wear, preservation and/or low degradation of compounds contained in the composition, long staying power of an active agent delivered onto the skin and/or the hair.

The polyorganosiloxanes A according to the invention may in particular be used in compositions intended for the treatment of hair that has been exposed or that is being exposed to dye compositions comprising an oxidizing agent, typically compositions for lasting dyeing, comprising an oxidation base or compositions for bleaching or lightening the hair, comprising an oxidizing agent. In this regard, this may include a shampoo, a conditioner, or a composition for treating or conditioning the hair after dyeing.

The composition according to the invention may be a composition for dyeing the hair. Such compositions are known to a person skilled in the art. It is specified that the compositions for dyeing the hair may consist of several hair dyeing products intended to be mixed by the user. In the present application, unless otherwise stated or unless specified, the term "composition for dyeing the hair" covers both a complete composition, or a product intended to be mixed with another by the user. In the present application, the term "hair dyeing" covers any modification of the color of the hair, whether this is dyeing proper, bleaching or a combination of bleaching and dyeing.

The composition for dyeing the hair may comprise an oxidation base (oxidation dye precursors). It may comprise an oxidizing agent. It may comprise a coupling agent (color modifier). It may comprise a direct dyeing agent (direct dyes). The composition comprises a cosmetically acceptable vector. The composition may also comprise adjuvants.

According to one embodiment, it is a composition for a long-lasting dyeing comprising an oxidation base, an oxidizing agent, and optionally a coupling agent, preferably in the form of two products to be combined, one product comprising the oxidation base and one product comprising the oxidizing agent.

According to one embodiment, it is a composition for temporary or long-lasting dyeing comprising a direct dyeing agent, and optionally an oxidizing agent.

According to one embodiment, it is a composition for bleaching or lightening the hair, comprising an oxidizing agent.

By way of direct dyeing agents, there may be mentioned neutral, acidic or cationic nitrobenzene dyes, neutral, acidic or cationic azo direct dyes, neutral, acidic or cationic quinone and in particular anthraquinone direct dyes, azine direct dyes, methine direct dyes, tetraazapentamethine direct dyes, triarylmethane direct dyes, indoamine direct dyes and natural direct dyes.

As oxidizing agents, there may be mentioned hydrogen peroxide, urea peroxide, alkali metal bromates, persalts such as perborates and persulfates, peracids and enzymes, in particular peroxidases, oxidoreductases containing 2 electrons, and oxygenases containing 4 electrons.

As coupling agents, there may be mentioned meta-phenylenediamines, meta-aminophenols, meta-diphenols, naphthalene couplers and heterocyclic couplers.

As cosmetically acceptable vectors which are preferred in the dye compositions, there may be mentioned water and/or mixtures thereof with solvents, for example ethanol, isopropanol, polyols and polyol ethers such as 2-butoxyethanol, propylene glycol, aromatic alcohols such as benzyl alcohol or phenoxyethanol.

The adjuvants may be anionic, nonionic, cationic or zwitterionic or amphoteric surfactants, anionic, neutral or cationic polymers, inorganic or organic thickening agents, antioxidants, penetrating agents, sequestering agents, perfumes, buffers, dispersing agents, conditioners, film-forming agents, ceramides, preservatives, opacifiers. Of course, the ingredients mentioned above may be used as adjuvants in the compositions for dyeing.

The compositions for dyeing the hair comprising the polyorganosiloxanes A according to the invention can thus:
   prevent lightening of the coloration over time (fading),
   promote fastness of the coloration over time,
   reduce extraction of the color, and/or
   repair the hair with respect to oxidation.

In the sun protection products, comprising UV-screening agents, for example antisun creams, milks, oils, sprays, the polyorganosiloxanes A according to the invention may themselves have a protective effect against the effects of UV radiation, on the skin and/or the hair. They may also have an effect of improving the protection of other agents, for example the UV-screening agents mentioned above, against the effects of UV radiation on the skin and/or on the hair (synergy between the polyorganosiloxanes A according to the invention and other agents). The protective effects against UV radiation may also be of benefit as regards maintaining the appearance or the performance of the composition over time (fewer degradations). Accordingly, the polyorganosiloxanes A according to the invention can avoid yellowing of the composition.

Of course, a specialist will be careful to choose the possible compound(s) to be added to the composition according to the invention such that the advantageous properties intrinsically attached to the composition in accordance with the invention are not, or not substantially, impaired by the addition envisaged.

According to a preferred embodiment, the cosmetic compositions devoid of toxicity upon skin contact according to the invention are used as a care and/or hygiene product for a keratin material such as the skin, the scalp, the hair, the eyelashes, the eyebrows, the nails or the mucous membranes.

According to another preferred embodiment, the cosmetic composition devoid of toxicity upon skin contact according to the invention is characterized by the fact that it consists of a rinse-off or leave-in hair product for washing, dyeing, caring for, conditioning, straightening, maintaining the hairstyle or permanent or nonpermanent shaping of the hair, an antisun composition, a buccodental care product or a makeup product.

According to another embodiment of the invention, the cosmetic composition devoid of toxicity upon skin contact is characterized in that it is used as a rinse-off hair composition, in particular as a hairstyling and/or conditioning shampoo, or as a conditioner.

When the compositions in accordance with the invention are used as conventional shampoos, they are simply applied to wet hair and the foam generated by massaging or rubbing with the hands is then removed, after an optional exposure time, by rinsing with water, it being possible for the operation to be repeated once or several times.

The compositions of the invention may also be used as care or hygiene products such as protective, treatment or care creams for the face, for the hands or for the body, protective or care body milks, lotions, gels or foams for caring for or cleansing the skin.

The compositions of the invention may also be used as antisun compositions.

The compositions may also consist of solid preparations constituting cleansing soaps or cakes.

The compositions may be makeup products such as creams for the face, foundations, mascaras, eyeliners, lipsticks, nail varnishes.

In the compositions according to the invention, the polyorganosiloxanes A may represent from 0.001% to 10% by weight, preferably from 0.01% to 5% by weight and more particularly from 0.1% to 3% by weight relative to the total weight of the final composition.

Another subject of the invention consists of a method for the cosmetic nontherapeutic treatment of the skin, the scalp, the hair, the eyelashes, the eyebrows, the nails or the mucous membranes, characterized in that a composition according to the invention, and as defined above, is applied to the keratin support, according to the customary technique for using this composition.

Another subject of the invention consists of a cosmetic use of a composition according to the invention and as defined above for the cleansing and/or care and/or conditioning and/or styling of the hair.

Another subject of the invention consists of a use of the polyorganosiloxanes A according to the invention and as described above for cleansing and/or care and/or conditioning and/or styling of the hair.

Finally, the last subject of the invention consists of a method of cosmetic treatment, comprising the application to the hair of an effective quantity of a cosmetic composition according to the invention and as described above.

Concrete, but not at all limiting, examples illustrating the invention will now be given.

EXAMPLES

Example 1

Preparation of Polyorganosiloxanes Ax Devoid of Toxicity Upon Skin Contact According to the Invention Oil 1: $\alpha,\omega$-bis(trimethylsilyl)-poly[dimethyl, methyl [3-(2,2,6,6-tetramethylpiperidin-4-yloxy)propyl]siloxane, (Rhodorsil® 21645 oil provided by the company Bluestar Silicones France)—viscosity: 10 000 mPa·s.

Oil 2: $\alpha,\omega$-bis(trimethylsilyl)-poly[dimethyl, methyl [3-(2,2,6,6-tetramethylpiperidin-4-yloxy)propyl]siloxane, (Rhodorsil® 21650 oil provided by the company Bluestar Silicones France)—viscosity: 90 000 mPa·s.

For oils 1 and 2, before the treatment according to the invention, the level of oligomers having a molecular mass M<1000 Daltons is of the order of 2 to 2.6% relative to the total molecular distribution.

Method of "extensive devolatilization" according to the invention: The oil is loaded into a reactor, mechanically stirred and gradually heated to 170° C. (using a heat transfer fluid which carries heat across the wall of the apparatus). The level of oligomers (having a molecular mass M<1000 Daltons) is reduced by extensive devolatilization under reduced pressure (about 4 mbar) for a sufficient period so that it is less than 1%. The level is determined by gel permeation chromatography (GPC).

The results are presented in table II.

TABLE II

Characteristics of the oils according to the invention

|  | Raw material = Oil 1 (Rhodorsil® 21645) | | | Raw material - Oil 2 (Rhodorsil® 21650) | | |
| --- | --- | --- | --- | --- | --- | --- |
| Polyorganosiloxanes Ax devoid of toxicity upon skin contact (containing a sterically hindered piperidinyl functional group) according to the invention (after extensive devolatilization) | A1 | A2 | A3 | A4 | A5 | A6 |
| Devolatilization time (h) at 4 mbar | 3 | 6 | 9 | 3 | 6 | 9 |
| Level of the oligomers having a molecular mass M < 1000 Daltons relative to the total molecular distribution | 0.90 | 0.65 | 0.55 | 0.95 | 0.65 | 0.65 |
| Skin sensitization/LLNA test | Negative (not classified R43) | Negative (not classified R43) | Negative (not classified R43) | Negative (not classified R43) | Negative (not classified R43) | Negative (not classified R43) |

Results of the LLNA Test ("Local Lymph Node Assay"):

This test is performed for each oil A1 to A6 according to the invention and for the oils 1 and 2 (comparatives) on mice and is based on the induction of the proliferation of lymphocytes in the ganglions subjacent to the site of application of the substance. Accordingly, the sensitizing power on the skin is evaluated (test in accordance with the guideline OECD 429 or the method described in annex V of the directive 67/548/EEC in its 29th adaptation to technical progress—2005/73/EC). The results show that the oils 1 and 2 are classified "R43" (sensitizing) whereas the oils A1 to A6 according to the invention are not classified "R43" (nonsensitizing).

Example 2

Preparation of Cosmetic Compositions (Shampoos)

Shampoo compositions were prepared, some in accordance with the invention (compositions I1, I2, I3, I4, I5 and I6) and the others comparative (compositions C1 and C2).

TABLE III

Compositions of the shampoos

| Constituents | Invention | | | | | | Comparative | |
|---|---|---|---|---|---|---|---|---|
| Sodium lauryl ether sulfate (C12/C14 at 70/30) at 2.2 mol of ethylene oxide | 11.2 g AM | 11.2 g AM | 11.2 g AM | 11.2 g AM | 11.2 g AM | 11.2 g AM | 11.2 g AM | 11.2 g AM |
| Cocoylbetaine at 30% of AM in aqueous solution | 5.1 g AM | 5.1 g AM | 5.1 g AM | 5.1 g AM | 5.1 g AM | 5.1 g AM | 5.1 g AM | 5.1 g AM |
| Lauryl ether carboxylic acid (4.5 EO) | 3 g AM | 3 g AM | 3 g AM | 3 g AM | 3 g AM | 3 g AM | 3 g AM | 3 g AM |
| Hydroxyethylcellulose crosslinked with epichlorohydrin and quaternized with trimethylamine, sold under the name JR400 by the company AMERCHOL | 0.7 g | 0.7 g | 0.7 g | 0.7 g | 0.7 g | 0.7 g | 0.7 g | 0.7 g |
| Polyorganosiloxane oils having sterically hindered piperidinyl functional groups (1.5 g AM) | A1 | A2 | A3 | A4 | A5 | A6 | Oil 1 | Oil 2 |
| Monoisopropanolamide of coprah acids | 2 g | 2 g | 2 g | 2 g | 2 g | 2 g | 2 g | 2 g |
| Preservatives, Perfume | q.s | q.s | q.s | q.s | q.s | q.s | q.s | q.s |
| Sodium hydroxide q.s | pH 5.3 | pH 5.3 | pH 5.3 | pH 5.3 | pH 5.3 | pH 5.3 | pH 5.3 | pH 5.3 |
| Demineralized water q.s | 100 g | 100 g | 100 g | 100 g | 100 g | 100 g | 100 g | 100 g |
| Compositions | I1 | I2 | I3 | I4 | I5 | I6 | C1 | C2 |

"AM" means active material

Shampooing is performed by applying the compositions I1, I2, I3, I4, I5 and I6 and the compositions C1 and C2 to the locks of previously wet sensitized hair. The shampoo is lathered, allowed to act for 10 minutes and then thoroughly rinsed with water. A panel of experts evaluated the appearance of the wet and dry hair.

Results: On wet hair, the compositions according to the invention I1, I2, I3, I4, I5 and I6 behave as well as the comparative compositions C1 and C2 more detached roots for the hair treated with the composition A according to the invention. On dry hair, the smoothing both visual and to the touch is improved for the hair treated with the composition A according to the invention.

Example 3

Preparation of Cosmetic Compositions (Shampoos) Comprising 2.5 g of Active Material of Polyorganosiloxane A Oil Having Sterically Hindered Piperidinyl Functional Groups According to the Invention The same compositions as those described in example 2 are prepared but with a quantity of 2.5 g of active material of oil having a piperidinyl functional group (A1 to A6) instead of 1.5 g for the compositions of the comparative trials. Indeed, because of the safety of the oils A according to the invention (not classified R43), it is now possible to formulate compositions having a concentration of oil with a piperidinyl functional group (A1 to A6) greater than the threshold of 2 g of active material.

TABLE IV

Compositions of the shampoos

| Constituents | Invention | | | | | | Comparative | |
|---|---|---|---|---|---|---|---|---|
| Sodium lauryl ether sulfate (C12/C14 at 70/30) at 2.2 mol of ethylene oxide | 11.2 g AM | 11.2 g AM | 11.2 g AM | 11.2 g AM | 11.2 g AM | 11.2 g AM | 11.2 g AM | 11.2 g AM |
| Cocoylbetaine at 30% of AM in aqueous solution | 5.1 g AM | 5.1 g AM | 5.1 g AM | 5.1 g AM | 5.1 g AM | 5.1 g AM | 5.1 g AM | 5.1 g AM |
| Lauryl ether carboxylic acid (4.5 EO) | 3 g AM | 3 g AM | 3 g AM | 3 g AM | 3 g AM | 3 g AM | 3 g AM | 3 g AM |
| Hydroxyethylcellulose crosslinked with epichlorohydrin and quaternized with trimethylamine, sold under the name JR400 by the company AMERCHOL | 0.7 g | 0.7 g | 0.7 g | 0.7 g | 0.7 g | 0.7 g | 0.7 g | 0.7 g |
| Polyorganosiloxane oils having sterically hindered piperidinyl functional groups (2.5 g AM) | A1 | A2 | A3 | A4 | A5 | A6 | Oil 1 | Oil 2 |
| Monoisopropanolamide of coprah acids | 2 g | 2 g | 2 g | 2 g | 2 g | 2 g | 2 g | 2 g |
| Preservatives, Perfume | q.s | q.s | q.s | q.s | q.s | q.s | q.s | q.s |
| Sodium hydroxide q.s | pH 5.3 | pH 5.3 | pH 5.3 | pH 5.3 | pH 5.3 | pH 5.3 | pH 5.3 | pH 5.3 |
| Demineralized water q.s | 100 g | 100 g | 100 g | 100 g | 100 g | 100 g | 100 g | 100 g |
| Compositions | I7 | I8 | I9 | I10 | I11 | I12 | C1 | C2 |

The same tests as in example 2 are performed.

Results: On dry hair, the smoothing both visual and to the touch is improved for hair treated with the compositions I7 to I12 according to the invention compared with the compositions of the comparative trials (C1 and C2).

The invention claimed is:

1. A cosmetic nontherapeutic treatment of a keratin material, characterized in that a cosmetic and/or dermatological composition devoid of toxicity upon skin contact comprising in a cosmetically acceptable medium, at least one polyorganosiloxane A devoid of toxicity upon skin contact containing, per molecule, at least one siloxyl unit substituted with at least one functional group V comprising at least one sterically hindered piperidinyl functional group, said polyorganosiloxanes A being characterized in that, after their preparation, the level of monomers, oligomers and polymers having a molecular mass M<1000 Daltons is reduced to a value less than 1% relative to the total molecular distribution by means of a technique allowing selective separation of the monomers, oligomers and polymers having a molecular mass M<1000 Daltons is applied to said keratin material.

2. The method of claim 1, wherein the reduction of the level of monomers, oligomers and polymers having a molecular mass M<1000 Daltons is performed by extensive devolatilization under a reduced pressure between 3 and 20 mbar and a temperature between 100 and 210° C. until less than 1% of the total molecular distribution has a molecular mass M<1000 Daltons.

3. The method of claim 1, characterized in that the reduction of the level of monomers, oligomers and polymers having a molecular mass M<1000 Daltons is carried out by means of a batch reactor, a falling film evaporator, a scraped film evaporator, a centrifugal evaporator or a continuous flash evaporator.

4. The method of claim 1, characterized in that the polyorganosiloxane A contains, per molecule, at least one siloxyl unit substituted with at least one functional group V directly linked to a silicon atom, said functional group V being a group having one or more sterically hindered piperidinyl functional groups, selected from the group consisting of:

a) groups of formula (I):

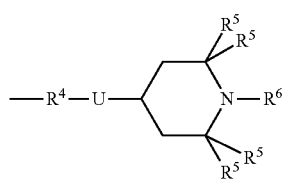

(I)

in which formula:
the radicals $R^5$, which are identical or different, are chosen selected from linear or branched alkyl radicals having 1 to 3 carbon atoms and the phenyl radical; and the radical $R^6$ represents a hydrogen radical, the radical $R^5$ or the O* atom;
$R^4$ is a divalent hydrocarbon radical chosen selected from the group consisting of:
linear or branched alkylene radicals having 2 to 18 carbon atoms;
alkylene-carbonyl radicals whose linear or branched alkylene part contains 2 to 20 carbon atoms;
alkylene-cyclohexylene radicals whose linear or branched alkylene part contains 2 to 12 carbon atoms and the cyclohexylene part contains an OH group and optionally 1 or 2 alkyl radicals having 1 to 4 carbon atoms;

the radicals of formula $R^7$—O—$R^7$ in which the radicals $R^7$, which are identical or different, represent alkylene radicals having 1 to 12 carbon atoms;
the radicals of formula $R^7$—O—$R^7$ in which the radicals $R^7$ have the meanings indicated above and one of them or both are substituted with one or two —OH groups;
the radicals of formula $R^7$—COO—$R^7$ in which the radicals $R^7$ have the meanings indicated above; and
the radicals of formula $R^8$—O—$R^9$—O—CO—$R^8$ in which the radicals $R^8$ and $R^9$, which are identical or different, represent alkylene radicals having 2 to 12 carbon atoms and the radical $R^9$ is optionally substituted with a hydroxyl radical; and U represents —O— or)-N($R^{10}$)—, $R^{10}$ being a radical chosen selected from the group consisting of a hydrogen atom, a linear or branched alkyl radical containing 1 to 6 carbon atoms and a divalent radical of the following formula (II):

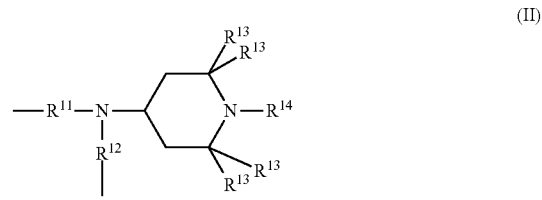

(II)

in which $R^{12}$ has the same meaning as for $R^4$ indicated above, $R^{11}$ represents a linear or branched, divalent alkylene radical having from 1 to 12 carbon atoms, one of the valency bonds (that for $R^{11}$) being linked to the atom of —$NR^{10}$—, the other (that for $R^{12}$) being linked to a silicon atom; the radicals $R^{13}$ are identical or different, chosen selected from the linear or branched alkyl radicals having 1 to 3 carbon atoms and the phenyl radical; and the radical $R^{14}$ represents a hydrogen radical, the radical $R^{13}$ or the O* atom; and b) groups of formula (III):

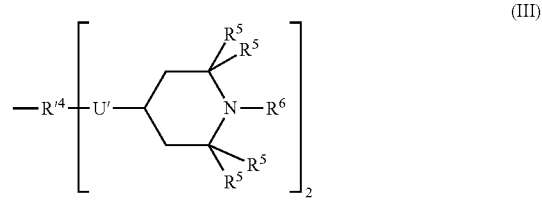

(III)

in which formula:
$R'^4$ is chosen selected from the group consisting of:
a trivalent radical of the following formula (IV):

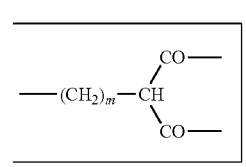

(IV)

where m represents a number from 2 to 20, and a trivalent radical of formula (VI):

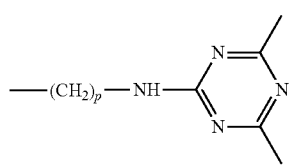

where p represents a number from 2 to 20,

U' represents —O— or —N($R^{12}$)—, $R^{12}$ being a radical chosen selected from the group consisting of a hydrogen atom and a linear or branched alkyl radical containing 1 to 6 carbon atoms; and $R^5$ and $R^6$ have the same meanings as those given in the case of the formula (I); said polyorganosiloxanes A are characterized in that after their preparations, the level of monomers, oligomers and polymers having a molecular mass M<1000 Daltons is reduced to a value less than 1% relative to the total molecular distribution by means of a technique allowing the selective separation of the monomers, oligomers and polymers having a molecular mass M<1000 Daltons.

5. The method of claim 1 characterized in that the functional group V is a propyloxytetramethylpiperidine radical of the following formula (X):

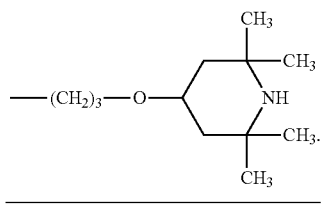

6. The method as claimed in claim 1, where in the polyorganosiloxane A 0.8 to 4% of the silicon atoms are substituted by a functional group V.

7. The method as claimed in claim 1, characterized in that the composition is in the form of an emulsion, lotion, gel, vesicular dispersion, paste, solid stick or is packaged as an aerosol and is provided in the form of a mousse or a spray.

8. The method as claimed in claim 1, wherein the keratin material is selected from skin, the scalp, the hair, the eyelashes, the eyebrows, the nails or the mucous membranes.

9. A method of use in cosmetics of a cosmetic and/or dermatological composition devoid of toxicity upon skin contact comprising in a cosmetically acceptable medium, at least one polyorganosiloxane A devoid of toxicity upon skin contact containing, per molecule, at least one siloxyl unit substituted with at least one functional group V comprising at least one sterically hindered piperidinyl functional group, said polyorganosiloxanes A being characterized in that, after their preparation, the level of monomers, oligomers and polymers having a molecular mass M<1000 Daltons is reduced to a value less than 1% relative to the total molecular distribution by means of a technique allowing selective separation of the monomers, oligomers and polymers having a molecular mass M<1000 Daltons, the method comprising cleansing and/or care and/or conditioning and/or styling of the hair with said composition.

10. The method as claimed in claim 9, characterized in that the composition is a rinse-off hair composition, a hairstyling and/or conditioning shampoo, or a conditioner.

11. The method as claimed in claim 9, characterized in that the composition consists of a rinse-off or leave-in hair product for washing, dyeing, caring for, conditioning, straightening, maintaining the hairstyle or permanent or nonpermanent shaping of the hair, an antisun composition, a buccodental care product or a makeup product.

12. A method of use of a polyorganosiloxanes A devoid of toxicity upon skin contact containing, per molecule, at least one siloxyl unit substituted with at least one functional group V comprising at least one sterically hindered piperidinyl functional group, said polyorganosiloxanes A being characterized in that, after their preparation, the level of monomers, oligomers and polymers having a molecular mass M<1000 Daltons is reduced to a value less than 1% relative to the total molecular distribution by means of a technique allowing selective separation of the monomers, oligomers and polymers having a molecular mass M<1000 Daltons, the method comprising cleansing and/or care and/or conditioning and/or styling of hair with said composition.

13. A method of preparing a polyorganosiloxane A devoid of toxicity upon skin contact containing, per molecule, at least one siloxyl unit substituted with at least one functional group V comprising at least one sterically hindered piperidinyl functional group, said polyorganosiloxanes A being characterized in that, after their preparation, the level of monomers, oligomers and polymers having a molecular mass M<1000 Daltons is reduced to a value less than 1% relative to the total molecular distribution by means of a technique allowing selective separation of the monomers, oligomers and polymers having a molecular mass M<1000 Daltons, comprising: performing a devolatilization step to selectively separate monomers, oligomers and polymers having a molecular mass M<1000 Daltons in a mixture of silicone oils, wherein the devolatilization step is performed at a temperature between 150° C. and 200° C. and under a reduced pressure between 3 mbar and 10 mbar.

14. A method as claimed in claim 13, wherein a duration of the devolatilization step is from 3 hours to 9 hours.

15. The cosmetic nontherapeutic treatment as claimed in claim 4, wherein the keratin material is skin, scalp, hair, eyelashes, eyebrows, nails or mucous membranes.

* * * * *